United States Patent [19]

Steffen

[11] 4,211,710
[45] Jul. 8, 1980

[54] PROCESS OF PREPARING 3-BROMOPHTHALIDE

[75] Inventor: Klaus-Dieter Steffen, Hennef, Fed. Rep. of Germany

[73] Assignee: Dynamit Nobel Aktiengesellschaft, Troisdorf bez. Cologne, Fed. Rep. of Germany

[21] Appl. No.: 901,917

[22] Filed: May 1, 1978

[30] Foreign Application Priority Data

May 11, 1977 [DE] Fed. Rep. of Germany ....... 2721142

[51] Int. Cl.² ............................................. C07D 307/88
[52] U.S. Cl. ........................ 260/343.3 R; 204/158 HA
[58] Field of Search ................... 260/343.3 R, 651 R, 260/343.6; 204/158 HA

[56] References Cited

U.S. PATENT DOCUMENTS

| 2,034,962 | 3/1936 | Smith et al. | 260/651 R |
|---|---|---|---|
| 2,430,822 | 11/1947 | Nevison et al. | 260/651 R |
| 3,223,728 | 12/1965 | Bella | 260/651 R |
| 3,350,467 | 10/1967 | Lasco | 260/651 R |
| 3,663,575 | 5/1972 | Roos et al. | 260/651 R |

OTHER PUBLICATIONS

Rabjohn, J. Amer. Chem. Soc., 76, 1954, pp. 5479–5481.
Wegner et al., Synthetic Organic Chem., John Wiley & Sons, Inc., p. 535 and p. 418.

*Primary Examiner*—Natalie Trousof
*Assistant Examiner*—Jane T. Fan
*Attorney, Agent, or Firm*—Sprung, Felfe, Horn, Lynch & Kramer

[57] ABSTRACT

3-Bromophthalide is produced by reaction of o-toluic acid with bromine or a bromine supplying substance according to the equation:

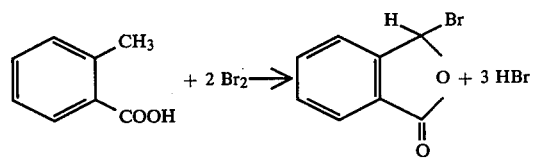

9 Claims, No Drawings

PROCESS OF PREPARING 3-BROMOPHTHALIDE

BACKGROUND

The invention concerns a method of preparing 3-bromophthalide, also called 3-bromo-1(3H)-isobenzofuranone, by the reaction of orthotoluic acid with bromine at elevated temperatures.

3-Bromophthalide is a known compound (Beilstein 17, p. 312, I p. 162, II p. 334) which can be prepared by the bromination of phthalide either with elemental bromine or with N-bromosuccinimide (Organic Syntheses 23 (1943) 74, 42 (1962) 26). By direct bromination, yields of 82 to 83% of the theory are obtained, but by bromination with N-succinimide yields of only 75 to 81% of the theory of 3-bromophthalide are obtained, and the product must then be recrystallized for purification.

Bromination with phthalic dialdehyde in carbon disulfide to 3-bromophthalide with only a 60% yield has been described by Simonis (Berichte 45 (1912) 1584).

Disadvantages of these methods are the insufficient purity, which can be improved by recrystallization with additional losses of yield, and the use of expensive starting substances which make these methods uneconomical.

THE INVENTION

It has been found that 3-bromophthalide can be prepared directly in a good yield and with a good purity of about 95% by the bromination of orthotoluic acid.

The subject of the invention is therefore a method of preparing 3-bromophthalide, which is characterized by reacting orthotoluic acid at elevated temperatures with bromine or substances yielding bromine with the formation off of hydrogen bromide.

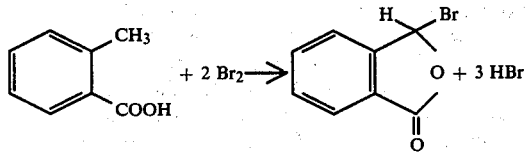

Orthotoluic acid is a chemical which can be manufactured cheaply by the unilateral air oxidation of orthoxylene.

It was not to be expected that the preparation of 3-bromophthalide in accordance with the above equation, which does not correspond to the conventional scheme of bromine substitution, could be achieved with high yields in a reaction that is simple to perform.

The high yields are achieved even though gas chromatography shows that during the reaction a series of by-products form which have been identified only partially. Surprisingly, the content of these by-products diminishes greatly towards the end of the bromination, and in the end product the substances are found either not at all or in very small amounts. Accordingly, the by-products that are formed are mainly only those which are transformed by bromination to bromophthalide.

The reaction is performed at temperatures between 70° and 260° C.

The bromination is performed preferably in the melt at temperatures between the melting point and the boiling point of the o-toluic acid, between 105° and 260° C. Preferably a range between 110° and 200° C. is selected, especially up to 180° C. Inert solvents can also be used, such as, for example, carbon tetrachloride, benzene, chlorinated benzenes, hexachlorobutadiene, etc., in which case the upper temperature limit is to be the boiling point of these solvents as long as the reaction is performed at standard pressure. In general, it is performed in an open vessel at standard pressure, although a slight overpressure is possible, with the purging off of the HBr that forms.

The reaction is a thermal bromination reaction which takes place rapidly at temperatures of about 130° C. or more, so that catalysts are not needed. At lower temperatures it is possible to use ultraviolet radiation or catalysts, examples of such catalysts being peroxides, such as benzoyl peroxide, dicumyl peroxide, or tertiary butyl peroxypivalate, or azo compounds such as azoisobutyric acid.

The bromine is put in generally in liquid form by introducing it through a tube under the surface of the stirred melt or solution. It is also possible to introduce bromine vapor, or inert gases such as nitrogen, helium or carbon dioxide charged with bromine, into the melt.

The use of BrCl instead of bromine is possible, in which case the exhaust gas will then consist of HCl instead of HBr. Other bromine donors are also usable, such as N-bromosuccinimide or, in some cases, bromides of phosphorus.

Bromine can be added in the molar ratio of from 1:2 to about 1:2.2

Bromine is used with a slight excess of 0.5 to 5.0% above the calculated value in order to compensate for the bromine losses in the hydrogen bromide exhaust gas. A greater excess of bromine is to be avoided, since otherwise large amounts of phthalic acid anhydride are formed.

After the end of the reaction the raw mixture is usually distilled in vacuo (116°–118° C. at 5 Torr) with the removal of a small amount of first runnings. The first runnings will contain possibly toluic acid, phthalide, and phthalic acid anhydride.

The other method of working up the raw mixture is to recrystallize the raw mixture from solvents and to reuse the mother liquors, if desired. For example, the recrystallization can be performed in 10 to 15 parts of cyclohexane or 1 part of toluene for each part of raw mixture, or from mixtures of aliphatic and aromatic hydrocarbons.

With recrystallization, the yield of bromophthalide is slightly poorer and the color of the end product somewhat darker, but the purity is better.

Even small percentages of accompanying substances bring about a great depression of the melting point, so that a lower melting point does not necessarily signify poorer quality. Normally, melting ranges of 75° to 80° C. are obtained, whereas in the case of recrystallization they are around 80° to 85° C.

In the absence of moisture and at a relatively cool temperature, 3-bromophthalide is stable for some time. The access of light and traces of metal such as iron or iron compounds can lead to decomposition phenomena, which can be be lessened by the addition of very small amounts of complexing agents such as nitrilotriacetic acid, or aminopolycarboxylic acids such as ethylenetetraacetic acid or their salts.

Any impurities which might remain in the 3-bromphthalide prepared by the present method will not interfere with its use for the introduction of the phthalidyl radical.

The exhaust gases consist of dry hydrogen bromide which contains only traces of bromine. Bromine can be recovered from the hydrogen bromide by means, for example, of chlorine or hydrogen peroxide. Direct consequent reactions, such as transhalogenations, e.g., the conversion of chlorine compounds to bromine compounds, can be performed with this hydrogen bromide gas.

3-Bromophthalide can be used in the preparation of penicillin, ampicillin and cephalosporin phthalidyl esters (DT-OS 22 25 149, 22 28 012, 23 64 749, 23 64 759, 24 49 863, 22 28 255, 25 07 374, Japanese Patent Nos. 73-97895 and 74-30388, and Great Britain Pat. No. 1,377,817), from which fungicidal phthalidyldialkyldithiocarbamates are made (Japanese Patent No. 73-11012), or it can be used generally in organic synthesis for the introduction of the phthalidyl radical.

EXAMPLES

EXAMPLE 1

408.4 g of orthotoluic acid (3 moles) is melted in a four-necked flask, equipped with stirrer, cooler, thermometer and dropping funnel, and heated at 140° C. 1007 g of bromine (6.3 moles) is added drop by drop over a period of 8 hours, and distributed by stirring.

Crude yield: 619 g (96.8% of the theory).

The product is distilled at a vacuum of 4 Torr. After taking out 25 g of first runnings, the main run is taken off at 116°–118° C., and the residue amounts to 23 g. Yield: 571 g (89.3% of the theory). M.P. 74°–79° C. Purity as determined by HBr titration after saponification: 95.8%.

EXAMPLE 2

Same as Example 1, but in a circulatory apparatus under irradiation from a Philips 300-Watt MLU bulb, 560.15 g of orthotoluic acid (4.12 moles) was reacted at 120° to 125° C. with 1440 g of bromine (9.0 moles) by feeding the latter in the form of bromine vapor through a valve at the foot of the apparatus. Crude yield: 875 g (99.6% of the theory). The product was dissolved in 900 ml of toluene while hot, cooled to −10° C., filtered and dried. Yield: 606 g (69.0% of the theory). M.P.: 80°–84° C. Purity: 96.7%.

An additional 20% of the theory of a 3-bromophthalide of lesser purity is to be obtained from the toluene filtrate.

EXAMPLE 3

In a four-necked flask equipped with stirrer, cooler, thermometer and a dropping funnel with a long neck, 136.14 g of orthotoluic acid (1 mole) was dissolved in 140 ml of orthodichlorbenzene and heated at 125° C. Under ultraviolet radiation, 331 g of bromine (2.07 moles) was added drop by drop over a period of 6 hours. 236 g of hydrogen bromide (97.2% of the theory) was intercepted. The solution was filtered while hot and cooled to −10° C. The precipitated crystals were filtered out and vacuum dried. Yield: 128 g (60.1% of the theory). M.P. 78°–85° C. Purity determined by titration: 97.8%.

By concentrating the filtrate to one-half and adding an equal amount of petroleum ether, an additional 41.3 g (19.4% of the theory) was obtained. M.P. 70°–79° C. Purity determined by titration: 90.8%.

What is claimed is:

1. Process of producing 3-bromophthalide which comprises contacting o-toluic acid with bromine or a substance supplying bromine at a temperature of 70° to 260° C. and for a time sufficient for formation of the 3-bromophthalide and HBr, the molar ratio of o-toluic acid to bromine being 1:2 to about 1:2.2, to produce the 3-bromophthalide from the o-toluic acid and bromine or substance supplying bromine in a single step.

2. Process of claim 1, wherein the o-toluic acid is contacted with bromine.

3. Process of claim 1, wherein the o-toluic acid is contacted with a substance-supplying bromine, said substance being BrCl or N-bromosuccinimide.

4. Process of claim 1, 2, or 3, wherein the o-toluic acid is a melt, and the temperature is 105° to 260° C.

5. Process of claim 1, 2, or 3, wherein the o-toluic acid is a melt, and the temperature is 110° to 200° C.

6. Process of claim 1, 2, or 3, said o-toluic acid being contained in an inert organic solvent.

7. Process of claim 4, wherein the molar ratio of o-toluic acid to bromine is 1:2 to about 1:2.2.

8. Process of claim 5, wherein the molar ratio of o-toluic acid to bromine is 1:2 to about 1:2.2.

9. Process of claim 6, wherein the molar ratio of o-toluic acid to bromine is 1:2 to about 1:2.2.

* * * * *